United States Patent [19]

Detweiler et al.

[11] 4,382,064

[45] * May 3, 1983

[54] SPECIMEN SLIDE FOR OCCULT BLOOD TESTING

[75] Inventors: Michael B. Detweiler, San Jose; Paul J. Lawrence, Campbell; Charles W. Townsley, San Jose, all of Calif.

[73] Assignee: SmithKline Instruments, Inc., Sunnyvale, Calif.

[*] Notice: The portion of the term of this patent subsequent to May 11, 1999, has been disclaimed.

[21] Appl. No.: 348,112

[22] Filed: Feb. 11, 1982

Related U.S. Application Data

[62] Division of Ser. No. 229,430, Jan. 29, 1981, Pat. No. 4,329,317.

[51] Int. Cl.³ ............................................. G01N 33/72
[52] U.S. Cl. ............................................ 422/58; 436/66
[58] Field of Search ....................... 23/230 B, 931, 932, 23/913; 422/55, 56, 57, 58; 436/66, 904

[56] References Cited

U.S. PATENT DOCUMENTS

| | | | |
|---|---|---|---|
| 3,252,762 | 5/1966 | Adams, Jr. et al. | 23/931 X |
| 3,853,471 | 12/1974 | Rittersdorf et al. | 422/56 X |
| 3,996,006 | 12/1976 | Pagano | 422/58 X |
| 4,071,321 | 1/1978 | Lam | 422/56 |
| 4,329,317 | 5/1982 | Detweiler et al. | 422/58 |

FOREIGN PATENT DOCUMENTS 2716060 10/1978 Fed. Rep. of Germany.

*Primary Examiner*—Arnold Turk
*Attorney, Agent, or Firm*—Joseph A. Marlino; Richard D. Foggio; Alan D. Lourie

[57] ABSTRACT

Specimen test slides for occult blood having a receiving sheet between a front panel and a rear panel with openings in the front and rear panels and pivotal covers coated with 2,6-di-tert-butyl-p-cresol to cover said openings.

4 Claims, No Drawings

SPECIMEN SLIDE FOR OCCULT BLOOD TESTING

This application is a division of copending Ser. No. 229,430, filed Jan. 29, 1981 which has issued into U.S. Pat. No. 4,329,317 on May 11, 1982.

Specimen test slides and procedures for detecting occult blood in fecal matter are well known. For example, U.S. Pat. No. 3,996,006 discloses slides having a specimen receiving sheet between a front panel and a rear panel with openings in the front and rear panels and pivotal covers or flaps to cover these openings. One such test slide is sold under the trademark of 'Hemoccult'.

The specimen receiving sheet is generally an absorbent paper impregnated with a guaiac reagent. The hemoglobin catalyzed oxidation of the guaiac extract coated paper is used clinically to detect occult blood in feces. Briefly, the test procedure is as follows.

A sample of fecal matter is smeared onto the guaiac paper through an opening of the front panel. The panel is then covered and the flap of the rear panel is opened. A developing solution such as hydrogen peroxide is applied to the guaiac paper via the corresponding opening in the rear panel. If blood is present in the fecal matter, the guaiac reaction will color the paper blue. The overall reaction is as follows:

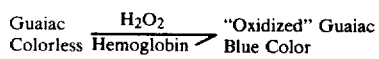

One of the major disadvantages of the guaiac test is that premature blueing occurs in the guaiac impregnated paper. Occasionally the paper will turn a slight blue color upon exposure to air. Trace amounts of nitrogen dioxide, ozone, and other oxidants in the air can penetrate the closed slide and react with the guaiac in the paper to cause a blue coloration. This premature blueing can introduce an element of confusion in the test and result in false positive tests.

Previous attempts have been made to stabilize the guaiac impregnated paper. Some commercial test slides place glazine paper over the openings in the front panel to protect the guaiac paper when the slide is exposed to the atmosphere. German Offenlegungschrift 2,716,060 discloses a method of treating the paper with various antioxidants. The results of this test revealed that the paper treated at protective antioxidant concentrations was not useful in detecting pathological amounts of blood in feces because the sensitivity of the test was negatively influenced. When the concentrations of antioxidants were reduced so that a sufficient sensitivity of the test was reached, the substances lost their stabilizing action.

Offenlegungschrift 2,716,060 reported that of all the compounds tested, the 1-arylsemicarbazides, specifically 1-phenylsemicarbazide, gave some degree of protection when impregnated on the guaiac paper. However, 1-phenylsemicarbazide also increases the bleaching of the blue color produced in a positive test.

It is therefore the object of this invention to stabilize the guaiac impregnated paper by preventing premature blueing without essentially influencing the sensitivity of the test.

Unexpectedly, it was discovered that when 2,6-ditert-butyl-p-cresol (BHT) was coated on the cover or flap of the slide and not impregnated in the guaiac paper, the paper was stable against premature blueing caused by light and air and pathological amounts of blood in feces were easily detectable.

Several major advantages result in coating the slide cover or container instead of impregnating the guaiac paper with the antioxidants. Due to the small concentration of antioxidant required, the material can be applied by dissolving and/or suspending it in the thin film of varnish that is normally employed to prevent ink smearing during manufacture. Further, once the antioxidant is added to the coating varnish there is no change in the manufacturing procedure. This approach is very cost effective. Most important, since no additional material is introduced into the guaiac paper, the performance of the slide remains unchanged.

A number of antioxidants were tested for their ability to prevent premature blueing of 'Hemoccult' slides by coating the slide, specifically the inside flap or cover. The test procedure was as follows:

Six antioxidants were dissolved in acetone, 22.5μ moles of each were then applied to the inside cover of the slides. After all the solvent evaporated the slides were closed to simulate an unopened 'Hemoccult' slide. The slides were then exposed to nitrogen dioxide in air, 2 ppm. The blueing time of each slide was noted. Following are the results:

| Compound | Blueing Time* |
|---|---|
| Control (acetone alone) | 5 minutes |
| Vanillin | " |
| 1-phenylsemicarbazide | " |
| 4-phenylsemicarbazide | " |
| 4-phenyl-3-thiosemicarbazide | " |
| 3,3-thiodipropionic acid | " |
| BHT | 240 minutes |

The results clearly demonstrate that under exaggerated conditions, when BHT is coated on the slide cover, the guaiac paper is protected against blueing. It will be noted that although 1-phenylsemicarbazide has been reported to give some degree of protection when applied directly to the guaiac paper, it has no effect when coated on the inside cover of the slide.

BHT was dissolved in varnish, applied to the inside cover of a slide and the closed slide exposed to air under normal conditions. Following are the results of this test:

| mg. BHT Applied | Blueing Time* |
|---|---|
| 0 | 2 days |
| 0.6 | 20 days |
| 1.5 | 27 days |

*Blueing time is defined as the time when the first tinge of blue is noted.

The results again demonstrate that BHT dissolved in varnish has a protective effect on the guaiac paper when coated on the cover of the test slide.

The BHT may be dissolved or suspended in a suitable organic solvent such as acetone or alcohol and applied to the cover flaps. Advantageously, varnish, which is a solution of a resin or drying oil in a volatile solvent, is employed as the carrier for the BHT. The varnish solution is coated or printed on the slide covers and not applied to the guaiac paper.

Preferably solutions or suspensions containing up to five percent by weight of BHT may be employed. Most advantageously, solutions of about 2 to 3 percent are employed.

The following examples are not limiting but are illustrative of this invention.

EXAMPLE 1

| Ingredients | Amounts |
|---|---|
| 2,6 di-tert-butyl-p-cresol (BHT) | 10 gms. |
| Varnish | 454 gms. |

BHT was dissolved in the varnish and printed on the inside cover slides of a 'Hemoccult' test slide.

The varnish was comprised of a phenolic resin, China wood oil, linseed oil, and alcohol.

EXAMPLE 2

| Ingredients | Amounts |
|---|---|
| 2,6-di-tert-butyl-p-cresol (BHT) | 10 gms. |
| Acetone | 454 gms. |

BHT was dissolved in the acetone and coated on the slide cover of a 'Hemoccult' slide.

What is claimed is:

1. In a specimen test slide for occult blood having a front panel, a rear panel, said front panel having a plurality of openings, a specimen receiving sheet carrying a guaiac test reagent between the front and rear panels, pivotal covers in said front and rear panels opposite said openings, the improvement comprising: said pivotal covers being coated with a composition containing 2,6-di-tert-butyl-p-cresol.

2. The slide of claim 1 wherein the inside cover of the slide is coated.

3. The slide of claim 2 wherein the composition is a varnish solution or suspension.

4. The slide of claim 3 wherein the 2,6-di-tert-butyl-p-cresol is present from about 2 to about 3 percent by weight in the composition.

* * * * *